United States Patent

Berberich

(10) Patent No.: US 9,274,034 B2
(45) Date of Patent: Mar. 1, 2016

(54) PROCESSING APPARATUS FOR PROCESSING TISSUE SAMPLES HAVING A READING DEVICE FOR USER IDENTIFICATION UNITS

(71) Applicant: Leica Biosystems Nussloch GmbH, Nussloch (DE)

(72) Inventor: Markus Berberich, Heidelberg (DE)

(73) Assignee: Leica Biosystems Nussloch GmbH, Nussloch (DE)

(*) Notice: Subject to any disclaimer, the term of this patent is extended or adjusted under 35 U.S.C. 154(b) by 2 days.

(21) Appl. No.: 14/019,242

(22) Filed: Sep. 5, 2013

(65) Prior Publication Data

US 2014/0065662 A1    Mar. 6, 2014

(30) Foreign Application Priority Data

Sep. 6, 2012  (DE) .................. 10 2012 215 859

(51) Int. Cl.
  *A61B 10/00*  (2006.01)
  *G01N 1/31*  (2006.01)
  *G01N 1/06*  (2006.01)
  *G01N 35/00*  (2006.01)

(52) U.S. Cl.
  CPC .. *G01N 1/31* (2013.01); *G01N 1/06* (2013.01); *G01N 35/00871* (2013.01)

(58) Field of Classification Search
  CPC .................................. B01L 3/54; G01N 35/00
  USPC ......................................................... 422/536
  See application file for complete search history.

(56) References Cited

U.S. PATENT DOCUMENTS

| | | | |
|---|---|---|---|
| 6,800,249 B2 * | 10/2004 | de la Torre-Bueno | 422/63 |
| 7,783,383 B2 * | 8/2010 | Eliuk et al. | 700/245 |
| 2005/0159982 A1 * | 7/2005 | Showalter et al. | 705/2 |
| 2006/0199196 A1 * | 9/2006 | O'Banion et al. | 435/6 |
| 2007/0036686 A1 * | 2/2007 | Hatamian et al. | 422/102 |
| 2009/0057422 A1 | 3/2009 | Dugas et al. | |
| 2011/0304433 A1 | 12/2011 | Molewyk et al. | |
| 2012/0138499 A1 | 6/2012 | Berberich et al. | |

FOREIGN PATENT DOCUMENTS

| | | |
|---|---|---|
| DE | 4333949 A1 | 5/1995 |
| DE | 10041229 A1 | 3/2002 |
| DE | 10103948 A1 | 8/2002 |
| DE | 10318026 A1 | 11/2004 |
| DE | 102005033483 A1 | 2/2006 |
| DE | 102006023229 A1 | 11/2007 |
| DE | 102008052870 A1 | 7/2010 |

(Continued)

OTHER PUBLICATIONS

Leica SCN400, Leica Microsystems, Deutsch 914 710, 2009.

*Primary Examiner* — Jyoti Nagpaul
(74) *Attorney, Agent, or Firm* — Hodgson Russ LLP

(57) ABSTRACT

The invention relates to a processing apparatus (100) for processing tissue samples, having a control unit (140) configured to control at least one apparatus function of the processing apparatus (100); and a communication device (130, 135) configured to read at least one information item from a user identification unit (151, 152, 153) and convey the at least one information item to the control unit (140). The control unit (140) is configured to control the at least one apparatus function of the processing apparatus (100) based on the at least one information item conveyed.

11 Claims, 1 Drawing Sheet

(56) References Cited

FOREIGN PATENT DOCUMENTS

| DE | 102005057191 | B4 | 12/2011 |
| DE | 102011003375 | A1 | 8/2012 |
| WO | 2007115374 | A1 | 10/2007 |
| WO | 2008109672 | A1 | 9/2008 |
| WO | 2008156566 | A1 | 12/2008 |

* cited by examiner

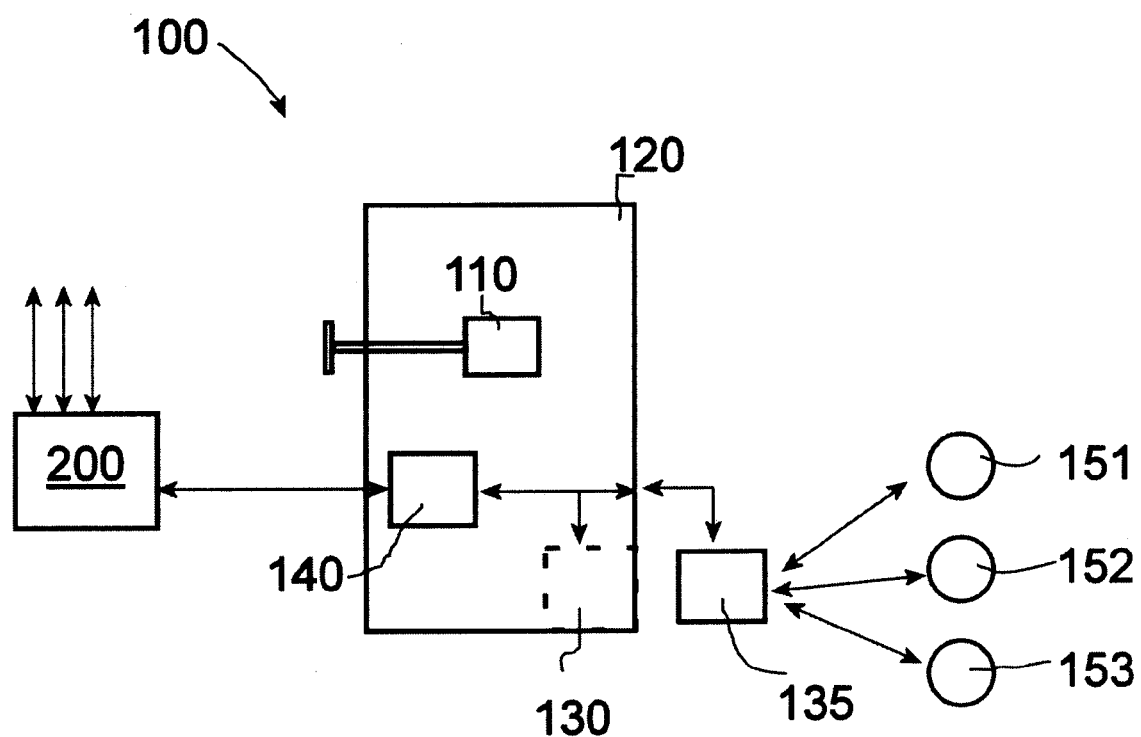

PROCESSING APPARATUS FOR PROCESSING TISSUE SAMPLES HAVING A READING DEVICE FOR USER IDENTIFICATION UNITS

CROSS REFERENCE TO RELATED APPLICATIONS

This application claims priority of German patent application number 10 2012 215 859.6 filed Sep. 6, 2012, the entire disclosure of which is incorporated by reference herein.

FIELD OF THE INVENTION

The present invention relates to a processing apparatus for processing tissue samples such as, for example, a microtome apparatus (e.g. cryostat microtome), a tissue processor, an automated stainer, or a scanning device for coverslipped specimen slides.

BACKGROUND OF THE INVENTION

DE 10 2008 052 870 A1 discloses a microtome apparatus having a capability for user identification. As a function of the user who is identified, for example, different apparatus functions can be authorized or blocked ("authentication"). Operator-specific apparatus settings associated with the user who is identified can also be transferred ("initialization").

It is desirable to simplify and accelerate user identification on such histological processing apparatuses, such as microtome apparatuses, and in particular to make it less susceptible to error, since such apparatuses are often used in a medical environment in which reliable and error-free operation is important.

SUMMARY OF THE INVENTION

The present invention proposes a processing apparatus for processing tissue samples, having the features disclosed herein. Advantageous embodiments are the subject matter of the description that follows.

In histology, in addition to microtomes for the production of tissue sections, various automatic processing machines such as, for example, automated stainers (histostainers), as described for example in DE 100 41 229 A1; coverslippers, as described for example in DE 10 2011 003 375 A1, tissue processors, as described for example in DE 10 2005 057 191 B4; and scanning devices for coverslipped specimen slides, as described for example in the document "Leica SCN 400, Leica Microsystems, order number: Deutsch 914710, XII/09X, December 2009," are used for sample preparation Improved user identification is advantageous for all these processing apparatuses.

In the context of the invention, the processing apparatus is equipped with a communication device (hereinafter referred to as a "transceiver") which is set up to read out (and optionally to write) at least one information item from a user identification unit (hereinafter referred to as a "transponder"). Communication between the transceiver and the transponder preferably takes place wirelessly. The at least one information item serves to identify the user. The transceiver can comprise a reading device or a reading/writing device. The transponder can accordingly be read or can be read and written to. The at least one information item can be, in particular, a user identifier (e.g. a character sequence).

The invention appreciably simplifies user identification on histological processing apparatuses. Error susceptibility decreases, and incorrect inputs can be avoided. The identification can preferably be combined with an authentication and/or initialization. The entire procedure can be configured so that it proceeds substantially automatically. Transponders are preferably read out and/or written to wirelessly and an RFID system made up of RFID transceivers and RFID transponders is used. RFID transponders exist as very small units, so that they can easily be carried along by users. A further advantage of RFID transponders is the low cost of manufacture and acquisition, as well as their robustness and reliability, which improves utilization capability in particular in the medical sector, in which chemicals, etc. are often dealt with.

The invention makes possible simple association of the processing action with the executing user. This is advantageous in particular for documentation purposes. A kind of logbook regarding processing can be kept. This is very advantageous in particular for the medical sector, since it is thereby possible to determine who processed which tissue at what point in time. The processing apparatus (in this case in particular the control device thereof) is preferably set up to store, preferably within a memory device of the processing apparatus and/or in a connected calculator unit, data regarding a processing action carried out on a tissue, together with an information item read out from a transponder and preferably a sample identification. A logbook function can thereby be created in simple fashion.

Besides the user identification information, further information items can be contained in the transponder, for example the aforementioned operator-specific setting values for initialization of the processing apparatus. The further information items can, however, also be stored in the processing apparatus itself and/or in a higher-order control system, and can be linked to the user identification information. They are then read in from the corresponding location by means of a loading function when the user has identified himself or herself on the processing apparatus by way of the transponder.

Further advantages and embodiments of the invention are evident from the description and from the attached drawings.

It is understood that the features recited above and those yet to be explained below are usable not only in the respective combination indicated, but also in other combinations or in isolation, without departing from the scope of the present invention.

BRIEF DESCRIPTION OF THE DRAWINGS

For a fuller understanding of the nature and objects of the invention, reference should be made to the following detailed description taken in conjunction with the accompanying drawings, in which:

FIG. 1 is a schematic block view of a preferred embodiment of a processing apparatus according to the present invention.

DETAILED DESCRIPTION OF THE INVENTION

The invention is schematically depicted in the drawings on the basis of an exemplifying embodiment and will be described in detail below with reference to the drawings.

The present invention is described substantially in connection with microtomes. It is nevertheless suitable and advantageous in general for processing apparatuses in histology.

A preferred embodiment of a processing apparatus according to the present invention is shown in FIG. 1 in a schematic block view, and is labeled 100 in its entirety. Processing apparatus 100 is embodied here as a cryostat microtome, a microtome 110 being arranged in a cryostat 120. Reference may be made, for example, to DE 103 18 026 A1 regarding further details of a cryostat microtome.

A communication device embodied here as an RFID transceiver is provided, built into cryostat microtome 100 (labeled 130) or separately therefrom as an independent module (labeled 135). This communication device is communicatively connected to a control device 140 of cryostat microtome 100. The control device 140 is set up to control apparatus functions of cryostat microtome 100 such as, for example, data reading and writing functions, cooling functions, sectioning functions, illumination functions, sample transport and handling functions, or locking of a cover. Control device 140 is further set up for a logbook function.

The RFID transceiver is set up to interact with identification units embodied here as RFID transponders 151, 152, 153. Stored in each transponder is at least one information item ("user identifier") that permits an unequivocal identification of the respective transponder 151, 152, 153. and thus of the user possessing the respective transponder.

Control device 140 is set up to interact with RFID transceiver 130, 135. Different stages of interaction are envisaged here. In a simple embodiment, only the information item that is read out is logged and stored in a logbook function. This serves as identification of the user operating cryostat microtome 100. This information item can be stored together with other information items that may be present, for example information items regarding processed tissue samples, information items regarding apparatus settings, environmental influences, etc.

In a further embodiment, control device 140 is set up, alternatively or additionally thereto, to authorize and block apparatus functions as a function of the information item that is read out. This serves for authentication of the user, with the result that, for example, sensitive or hazardous apparatus functions can be authorized only for experienced or specific users.

In a further preferred embodiment, control device 140 is set up, alternatively or additionally thereto, to establish user-specific apparatus settings as a function of the information item that is read out. The user-specific apparatus settings can likewise be stored in transponder 151, 152, 153, in control device 140, and/or in a higher-order control system 200 that is optionally in communication with further processing apparatuses, and loaded from there.

It is to be emphasized that any combination of the functions just explained is possible.

The invention is not to be limited to the specific embodiments disclosed, and modifications and other embodiments are intended to be included within the scope of the invention.

What is claimed is:

1. A processing apparatus (100) for processing tissue samples, the processing apparatus comprising:
a control unit (140) configured to provide a logbook function and to control at least one apparatus function of the processing apparatus (100), wherein the at least one apparatus function comprises at least one of the group consisting of a data reading and writing function, a cooling function, a sectioning function, an illumination function, a sample transport and handling function, and locking of a cover, and wherein the processing apparatus (100) comprises an apparatus selected from a group consisting of a microtome, an automatic stainer, a coverslipper, a tissue processor, and a scanning device for coverslipped specimen slides; and
a communication device (130, 135) configured to read at least one information item from an RFID transponder in a user identification unit (151, 152, 153) and convey the at least one information item to the control unit (140);
wherein the control unit (140) includes a control system that is programmed to identify a user of the processing apparatus possessing the user identification unit and to control the at least one apparatus function of the processing apparatus (100) based on the at least one information item conveyed, wherein the control device (140) is configured to establish user-specific apparatus settings for initialization of the at least one apparatus function of the processing apparatus (100) as a function of the information item that is read out.

2. The processing apparatus (100) according to claim 1, wherein the logbook function includes a processing action carried out on a tissue sample and the user that performed the processing action.

3. The processing apparatus (100) according to claim 1, wherein the control system is further configured to enable the at least one apparatus function based on the at least one information item that is conveyed such that the user is authorized to perform the at least one apparatus function.

4. The processing apparatus (100) according to claim 1, wherein the control system is further configured to block the at least one apparatus function based on the at least one information item that is conveyed such that the user is not authorized to perform the at least one apparatus function.

5. The processing apparatus (100) according to claim 1, wherein the communication device (130, 135) comprises an RFID transceiver.

6. The processing apparatus (100) according to claim 1, wherein the communication device (130, 135) is integrated into the processing apparatus (100).

7. The processing apparatus (100) according to claim 1, wherein the communication device (130, 135) is physically separate from the processing apparatus (100).

8. A method for controlling an apparatus function of a processing apparatus (100) configured to process tissue samples, the method comprising:
wirelessly reading at least one information item from an RFID transponder in a user identification unit (151, 152, 153);
conveying the at least one information item from the user identification unit (151, 152, 153) to a control unit (140) of the processing apparatus (100), wherein the processing apparatus (100) comprises an apparatus selected from a group consisting of a microtome, an automatic stainer, a coverslipper, a tissue processor, and a scanning device for coverslipped specimen slides;
identifying a user of the processing apparatus possessing the user identification unit;
storing the at least one information item to a logbook;
establishing user-specific apparatus settings for initialization of the apparatus function of the processing apparatus (100) as a function of the at least one information item that is read out; and
controlling the apparatus function based on the at least one information item conveyed, wherein the apparatus function comprises at least one of the group consisting of a data reading and writing function, a cooling function, a sectioning function, an illumination function, a sample transport and handling function, and locking of a cover.

9. The method according to claim 8, wherein the storing includes a processing action carried out on a tissue sample and the user that performed the processing action.

10. The method according to claim 8, further comprising enabling the apparatus function based on the at least one information item that is conveyed such that the user is authorized to perform the at least one apparatus function.

11. The method according to claim 8, further comprising blocking the apparatus function based on the at least one information item that is conveyed such that the user is not authorized to perform the at least one apparatus function.

* * * * *